United States Patent [19]

Schmieding et al.

[11] Patent Number: 5,456,246
[45] Date of Patent: Oct. 10, 1995

[54] FAT PAD RETRACTOR

[75] Inventors: Reinhold Schmieding; Donald K. Shuler, both of Naples, Fla.

[73] Assignee: Arthrex, Inc., Naples, Fla.

[21] Appl. No.: 200,514

[22] Filed: Feb. 23, 1994

[51] Int. Cl.⁶ .................................. A61B 19/00
[52] U.S. Cl. ........................ 600/201; 606/151
[58] Field of Search ............... 606/1, 151, 139, 606/157, 141, 201, 222–228; 24/16 PB, 17 AB; 600/37; 128/20

[56] References Cited

U.S. PATENT DOCUMENTS

| | | | |
|---|---|---|---|
| 3,913,179 | 10/1975 | Rhee | 24/16 PB |
| 4,271,828 | 6/1981 | Angelchik | 600/37 |
| 4,730,615 | 3/1988 | Sutherland et al. | 24/16 PB |
| 4,950,285 | 8/1990 | Wilk | 606/151 |
| 5,226,429 | 7/1993 | Kurmak | 606/157 |
| 5,269,783 | 12/1993 | Sander | 606/222 |
| 5,337,736 | 8/1994 | Reddy | 128/20 |

OTHER PUBLICATIONS

C. A. Mills et al., "The Rubber Fat Pad Retractor: Use in Arthroscopic Anterior Cruciate Ligament Reconstruction," *Arthroscopy: The Journal of Arthroscopic and Related Surgery*, pp. 332–333 and contents page (Jun. 1993).

Primary Examiner—Stephen C. Pellegrino
Assistant Examiner—Glenn Dawson
Attorney, Agent, or Firm—Ostrolenk, Faber, Gerb & Soffen

[57] ABSTRACT

An apparatus and method for retracting the infrapatellar fat pad during arthroscopic knee surgery. The apparatus includes a silicone retractor strap for supporting the fat pad, a device for threading the strap into the arthroscopic operating compartment, and a segment of suture or other frangible connector for connecting the retractor strap to the threading device.

9 Claims, 4 Drawing Sheets

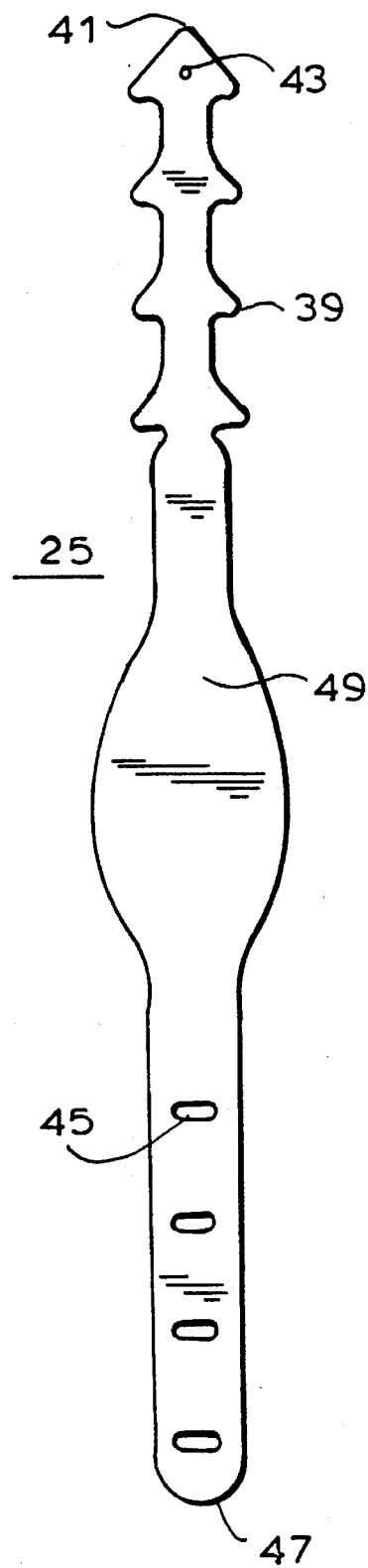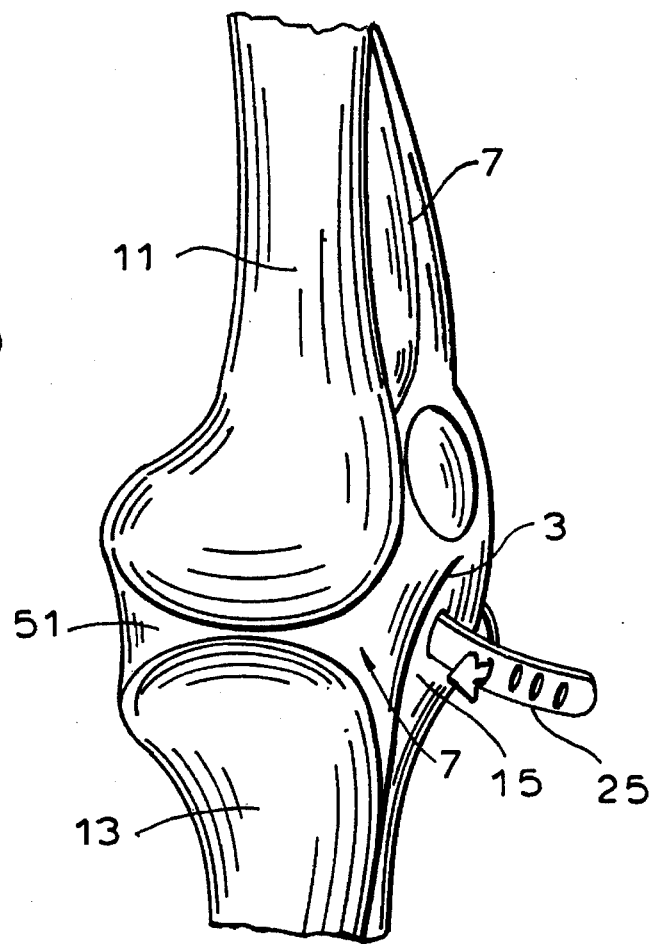

5,456,246

FAT PAD RETRACTOR

BACKGROUND OF THE INVENTION

1. Field of the Invention

The present invention relates to an apparatus and method for retracting tissue during surgery and, more specifically, to a fat pad retractor for use in anterior cruciate ligament (ACL) reconstruction.

2. Description of the Related Art

Successful arthroscopic surgery requires adequate visualization. During certain arthroscopic procedures, tissue structures within the operating compartment can obstruct the surgeon's view. Inadequate visualization often results in increased operating times and can also lead to damage of surrounding structures.

Referring to FIGS. 1 and 2, in arthroscopic knee surgery, particularly anterior cruciate ligament 1 reconstruction, the infrapatellar haversian pad of fat 3 obscures the intercondylar notch 5. Entry to the lateral compartment also can be impeded by the fat pad and the infrapatellar alar fold of synovium, a continuation of the suprapatellar bursa 7 which extends around the medial and lateral outer sides of the knee in the areas between the femur 11 and tibia 13.

Blocked visualization and impeded access can lead to damage of the fat pad 3 during surgery, which can result in an inadequate supply of blood to the patellar ligament 15. Gently retracting fat pad 3 can obviate risk to the intermeniscal ligaments, the anterior horns of the medial and lateral menisci, 17 and 19, respectively and the femoral condylar articular surfaces 21, 23. Retraction also increases the ability to have accurate sighting of the tibial locus for ACL reconstruction.

Accordingly, a need exists for a device and method to retract the fat pad during arthroscopic surgery.

SUMMARY OF THE INVENTION

The above-noted need is fulfilled by the present invention, which provides an apparatus and method for retraction of tissue, specifically the infrapatellar fat pad, during arthroscopic knee surgery. The retractor comprises a strap for supporting the tissue and a threading device for threading the strap into the arthroscopic operating compartment. The threading device is connected to the strap by a piece of suture.

Preferably, the strap is made of silicone. The strap can be trimmed to fit the tissue to be retracted. The ends of the strap can be connected outside the body both adjustably and lockably.

The method for retracting tissue during arthroscopic surgery includes creating two portals in the body and threading the retracting strap for supporting tissue into one portal, behind the tissue to be supported, and out through the other portal, such that the two ends of the strap extend out of each portal, and the tissue is supported from the back by a portion of the strap between the two ends. The two ends of the strap are pulled outwardly and locked together to retract the tissue.

The method of the present invention also preferably includes the preliminary steps of attaching the retracting strap to an obturator for threading the retractor into the body. The retractor and strap are connected together with a frangible material, preferably a segment of suture, which can be severed to provide easy release and removal of the obturator once the retractor is in position.

Other features and advantages of the present invention will become apparent from the following description of the invention with reference to the accompanying drawings.

BRIEF DESCRIPTION OF THE DRAWINGS

FIG. 5 is a detailed view of the retractor of the present invention.

FIG. 7 shows an anatomical cutaway view of the knee with the retractor in proper position and tightened.

DETAILED DESCRIPTION OF THE PREFERRED EMBODIMENT

Figure 3:
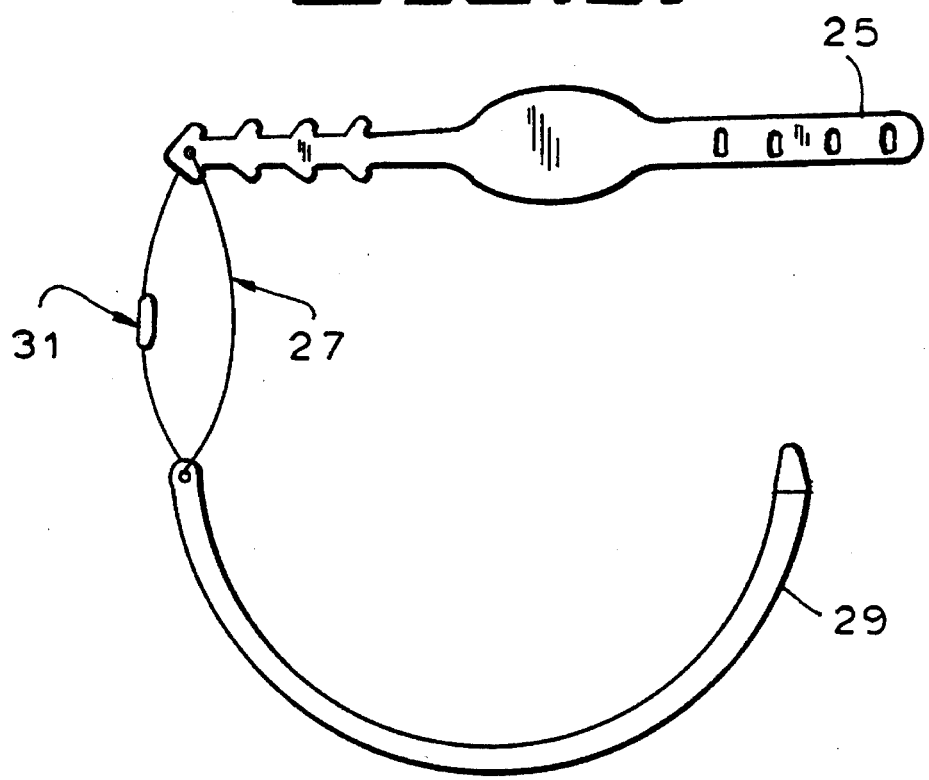
FIG. 3 shows the apparatus of the present invention, including a retractor and an obturator with connecting suture.

FIG. 3 shows the apparatus of the present invention comprising, in the preferred embodiment, a retractor strap 25 connected by suture 27 to an obturator 29. Suture 27 is preferably provided in a double strand, the ends of the suture being tied together with a knot and covered by a heat-shrink sleeve 31. Suture 27 is preferably number two braided silk suture having a length of approximately four inches, so that retractor 25 and obturator 29 are separated by approximately two inches when the apparatus is assembled.

Figure 4:
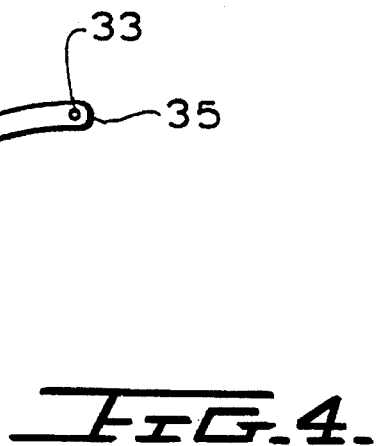
FIG. 4 is a detailed view of the obturator of the present invention.

Referring to FIG. 4, obturator 29 is an arcuate-shaped cylindrical plastic member formed of a surgically-acceptable plastic having a sufficient stiffness and flexibility to facilitate threading of the device through the patient's body. Obturator 29 is provided with an aperture 33 at its proximal end 35 and has a pencil-like point at its distal end 37. Aperture 33 receives suture 27 for coupling obturator 29 to the retractor 25. Pointed distal end 37 facilitates the threading of obturator 29 through the surgical cavity.

FIG. 5 shows retractor 25 in greater detail. Retractor 25 is formed of flexible silicone in the shape of a tie strap similar to that used, for example, in securing the opening of a trash bag. The distal end of retractor 25 has the shape of an arrow with a pointed head 41, followed by a plurality of locking wings 39, each of which has the shape of an arrowhead. An eye 43 is provided in pointed head 41 for receiving suture 27.

The proximal end of retractor 25 is provided with a plurality of lateral slots 45 adapted to first receive pointed head 41 and then successively receive one or more of the locking wings 39 when the device is being tightened following insertion, as discussed in greater detail below. The proximal end of retractor 25 has a rounded tip 47.

Retractor 25 is approximately five inches in length and includes an enlarged support area 49 centrally located between its ends. Support area 49 can be laterally trimmed to accommodate various sizes of fat pads.

Figure 2:
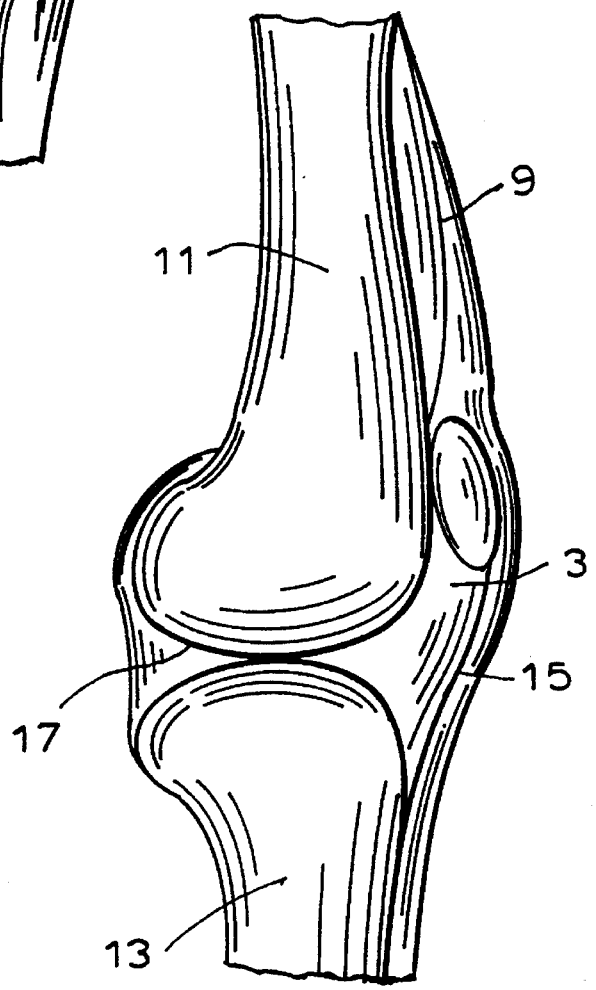
FIG. 2 is an anatomical, cutaway, lateral view of the knee showing its internal structures.
Figure 6:
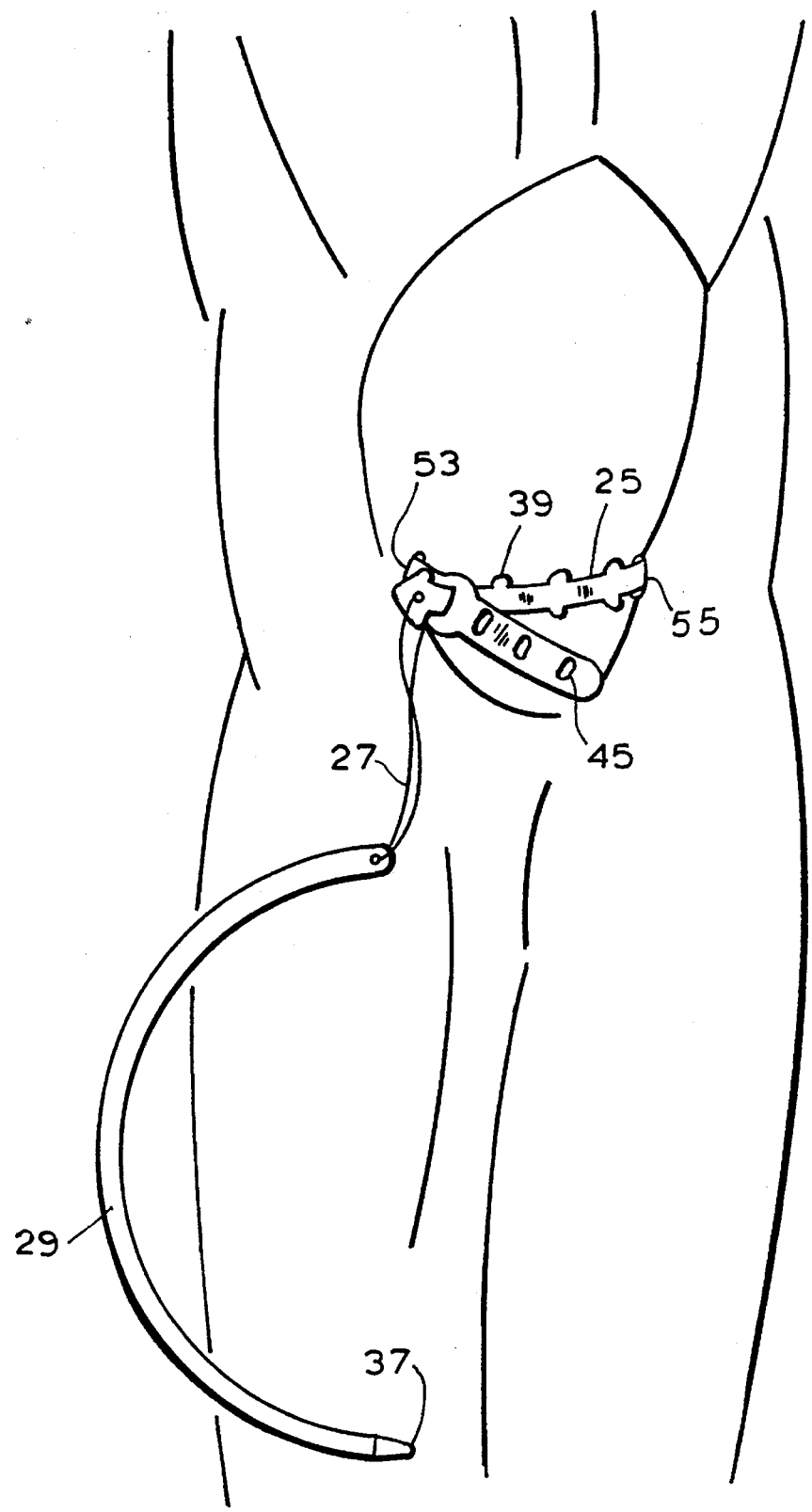
FIG. 6 is an exterior view of the knee showing the retractor of the present invention in place.

In the method of the invention, the distal end of obturator 29 is first inserted into the knee through a medial portal 53 formed behind infrapatellar fat pad 3 (FIGS. 2 and 6).

Obturator 29 is further advanced into the knee until its distal end 37 exits the knee through lateral anterior portal 55. The distal end of obturator 29 is then grasped by the surgeon and the remaining portion of the obturator, as well as suture 27 attached thereto, is pulled through the portals in the knee. As suture 27 exits the knee, retractor 25, coupled thereto, is drawn into the knee behind fat pad 3. Retractor 25 is advanced into the knee in this fashion until support area 49 lies directly behind fat pad 3.

When retractor 25 is in proper position with respect to fat pad 3 as described above, its distal end extends out of lateral anterior portal 55 and its proximal end extends out of medial portal 53. Then, as shown in FIG. 6, with the aid of obturator 29 as a threading device, the distal end of retractor 25 is inserted though one of the slots 45 in the proximal end of retractor 25, and the retractor is adjustably tightened by successively advancing locking wings 39 through slot 45. The arrowhead shape of the wings permits tightening of retractor, while at the same time preventing release thereof. After the retractor is tightened to the desired degree, suture 27 is cut to disconnect obturator 29, so that it can be removed from the surgical area outside the knee.

Figure 1:
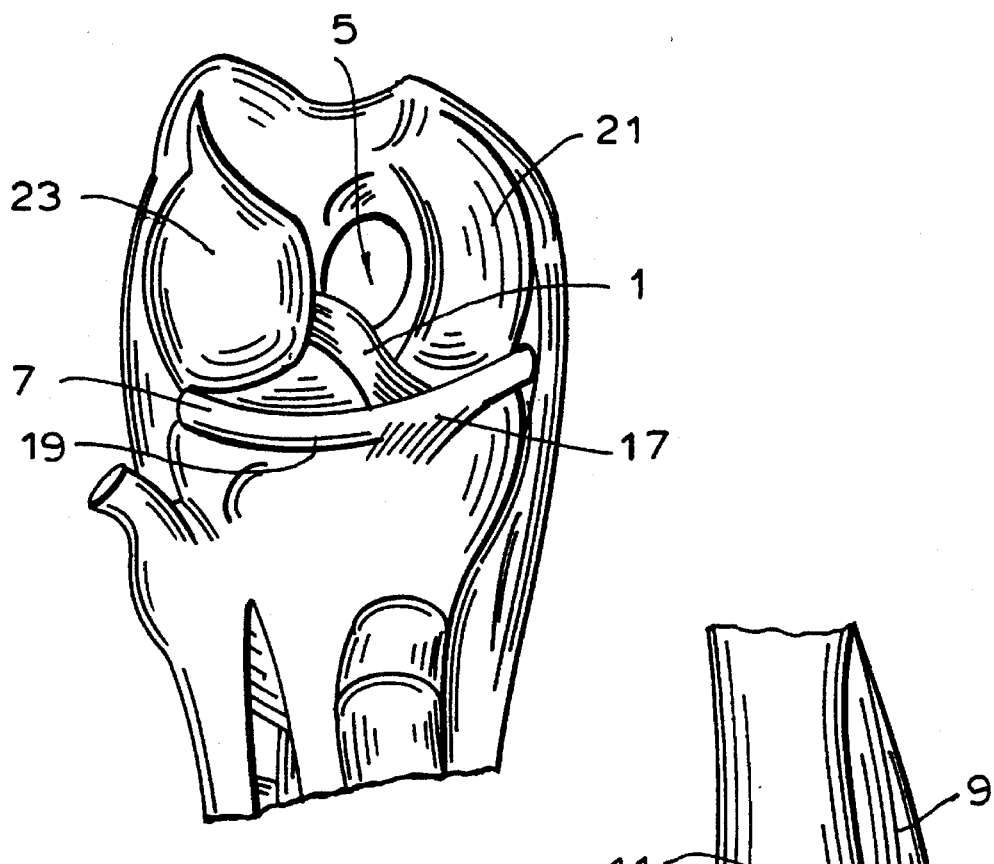
FIG. 1 is an anatomical, cutaway, anterior aspect of the knee showing its internal structures.

FIG. 7 is an anatomical view of the knee with retractor 25 properly inserted and tightened such that fat pad 3 is retracted from the lateral compartment 7, exposing the intercondylar notch 5 (FIG. 1) for arthroscopic surgery. Also shown in FIG. 7 are the subcutaneous prepatellar bursa 9 and the patellar ligament 15 which adjoin the fat pad 3 in the front of the knee. The medial meniscus 17 is located behind infrapatellar fat pad 3 and surrounds the abutting ends of the femur 11 and tibia 13.

The retraction of the fat pad in accordance with the present invention advantageously provides significantly improved visualization of the anterior space of the knee and facilitates the ease with which instruments can be inserted into the knee during arthroscopic surgery. Obviously, the device of the present invention can be used to retract tissue in a variety of other surgical procedures, such as shoulder surgery.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for retracting a fat pad during arthroscopic knee surgery, comprising:

a strap for retracting the fat pad, the strap comprising a proximal end, a distal end, a centrally disposed widened portion for supporting, inside the knee, the fat pad to be retracted, and means disposed on the proximal and distal ends which cooperate to adjustably and lockably connect the proximal and distal ends together outside the knee;

an obturator for threading the strap behind the fat pad to be retracted; and a closed loop of suture material connecting the strap to the obturator.

2. The apparatus of claim 1, wherein the strap is made of silicone.

3. An apparatus for retracting a fat pad during arthroscopic surgery, comprising:

a strap for retracting the fat pad, the strap having a proximal end, a distal end, and a widened support section between the proximal and distal ends for supporting, inside the knee, the retracted fat pad;

an arcuate-shaped cylindrical obturator for threading the strap behind the fat pad to be retracted; and a closed loop of suture material for connecting the threading member and the strap.

4. The apparatus of claim 3, wherein the obturator is formed of a surgically-acceptable plastic material.

5. The apparatus of claim 3, wherein the distal end of the strap includes an aperture for receiving the suture.

6. The apparatus of claim 3, wherein the distal end of the strap is formed in the shape of an arrow with a pointed head and the proximal end of the strap includes slots for receiving the pointed head of the distal end.

7. The apparatus of claim 6, wherein the distal end of the strap further comprises at least one locking wing, the locking wing having an arrowhead shape whereby, when the wing is drawn through one of the slots at the proximal end of the strap, the wing is locked to the proximal end of the strap.

8. A method for retracting a fat pad during arthroscopic knee surgery, the method comprising the steps of:

attaching a strap to an arcuate-shaped, cylindrical obturator with a closed loop of suture, the strap having a proximal end, a distal end, a centrally-disposed widened portion for supporting the fat pad to be retracted, and connecting means on the proximal and distal ends which cooperate to adjustably and lockably connect the proximal and distal ends together outside the knee;

threading the strap into the knee through a first portal, behind the fat pad to be retracted and out of the knee through a second portal, such that the distal end of the strap extends outside of the knee from the first portal, the proximal end of the strap extends outside of the knee from the second portal, and the central portion of the strap is disposed behind and supports the fat pad to be retracted;

connecting the proximal and distal ends of the strap together outside the knee using the connecting means provided on the proximal and distal ends; and adjusting the connection of the proximal and distal ends of the strap to retract the fat pad.

9. The method of claim 8, further comprising the step of detaching the strap from the obturator after the strap has been threaded into the knee by severing the suture material.

* * * * *